(12) United States Patent
Lee et al.

(10) Patent No.: US 11,786,852 B2
(45) Date of Patent: Oct. 17, 2023

(54) METHOD FOR PREDICTING PHYSICAL PROPERTIES OF AMORPHOUS POROUS MATERIAL

(71) Applicants: Hyundai Motor Company, Seoul (KR); Kia Motors Corporation, Seoul (KR); Seoul National University R&DB Foundation, Seoul (KR)

(72) Inventors: Jung Wook Lee, Gyeonggi-do (KR); Seong Je Kim, Gyeonggi-do (KR); Hyeong Rae Lee, Seoul (KR); Yeon June Kang, Seoul (KR); Sung Soo Yang, Seoul (KR)

(73) Assignees: Hyundai Motor Company, Seoul (KR); Kia Motors Corporation, Seoul (KR); Seoul National University R&DB Foundation, Seoul (KR)

( * ) Notice: Subject to any disclaimer, the term of this patent is extended or adjusted under 35 U.S.C. 154(b) by 737 days.

(21) Appl. No.: 16/990,449

(22) Filed: Aug. 11, 2020

(65) Prior Publication Data
US 2021/0325331 A1    Oct. 21, 2021

(30) Foreign Application Priority Data
Apr. 8, 2020   (KR) .................. 10-2020-0042832

(51) Int. Cl.
*B01D 39/16*   (2006.01)
*G16C 20/30*   (2019.01)
(Continued)

(52) U.S. Cl.
CPC ....... *B01D 39/1692* (2013.01); *G01N 23/046* (2013.01); *G16C 20/30* (2019.02); *G16C 60/00* (2019.02)

(58) Field of Classification Search
None
See application file for complete search history.

(56) References Cited

U.S. PATENT DOCUMENTS 6,256,600 B1 *   7/2001   Bolton ................. G10K 11/162
703/2

FOREIGN PATENT DOCUMENTS

JP            5222185 B2    6/2013
KR      10-1596373 B1    3/2016
(Continued)

*Primary Examiner* — Raul J Rios Russo
*Assistant Examiner* — Carl F. R. Tchatchouang
(74) *Attorney, Agent, or Firm* — Fox Rothschild LLP

(57) ABSTRACT

The present invention relates to a method for predicting physical properties of an amorphous porous material which may predict an acoustic physical property value and an absorption coefficient from parameters of an amorphous porous material, and may estimate the acoustic characteristics with the amorphous porous material which is an amorphous specimen even without separately producing a formalized specimen such as a cylindrical specimen or a flat specimen. Further, the method for predicting physical properties of the amorphous porous material may estimate the acoustic physical properties through the analysis of a three-dimensional pore connection structure, which is a microstructure of an amorphous specimen, even without acoustic impedance, thereby estimating the acoustic physical properties which accurately reflect the characteristics of the actual specimen.

14 Claims, 16 Drawing Sheets

(51) Int. Cl.
   *G16C 60/00*      (2019.01)
   *G01N 23/046*     (2018.01)

(56)            References Cited

FOREIGN PATENT DOCUMENTS

KR       10-1694905  B1    1/2017
KR       10-2067197  B1    1/2020
KR       10-2068765  B1    1/2020
KR       10-2068795  B1    1/2020

* cited by examiner

ENERGY DISSIPATION
DUE TO VISCOSITY

ENERGY DISSIPATION
DUE TO HEAT

METHOD FOR PREDICTING PHYSICAL PROPERTIES OF AMORPHOUS POROUS MATERIAL

CROSS-REFERENCE TO RELATED APPLICATION

This application claims under 35 U.S.C. § 119(a) the benefit of priority to Korean Patent Application No. 10-2020-0042832 filed on Apr. 8, 2020, the entire contents of which are incorporated herein by reference.

TECHNICAL FIELD

The present invention relates to a method for predicting physical properties of an amorphous porous material by obtaining acoustic physical property values and an absorption coefficient from parameters of an amorphous porous material.

BACKGROUND

There has been a problem in that in order to predict physical properties in the case of a porous material (for example, urethane foam), physical properties or performance is measured by directly making an actual object, and an operation of reproducing the actual object is repeated when not reaching the target, thereby increasing the time and the cost.

Accordingly, various prediction methods have been used, such that technologies of predicting physical properties or performance without directly making an actual object have been emerging. For example, there have been an impedance tube method for measuring acoustic performance by using cylindrical specimens having 29 mm and 100 mm in diameter of arbitrary thickness, a small reverberation chamber absorption coefficient measuring method for measuring acoustic performance by using flat specimens having 1 m in width and length of arbitrary thickness, and the like. However, since the prediction technologies are required to manufacture cylindrical or flat specimens, in the case of a porous material which has been already pre-shaped into a component, it is not possible to measure physical properties by introducing the prediction technology.

Accordingly, there is a need for a method capable of predicting physical properties such as acoustic physical properties even with a pre-shaped porous material, that is, an amorphous porous material.

The above information disclosed in this Background section is only for enhancement of understanding of the background of the invention and accordingly it may contain information that does not form the prior art that is already known in this country to a person of ordinary skill in the art.

SUMMARY

In preferred aspects, provided are methods for predicting physical properties of an amorphous porous material. The method may include obtaining acoustic physical property values and an absorption coefficient from a three-dimensional pore connection structure from a tomographic image of an amorphous porous material, and deriving parameters therefrom.

The term "amorphous porous material" as used herein refers to a porous material that includes plurality of shapes of pores (e.g., circular, or non-circular), holes, cavity (e.g., microcavity), labyrinth, channel or the like, without regularity or order therein. Exemplary amorphous porous materials may be formed from polymerizing monomers or copolymers, such as polyurethane, or formed naturally such as sponges, fabrics, ceramics, zeolites, corks, woods, and the like.

In an aspect, provided is a method for predicting physical properties of an amorphous porous material may include obtaining a parameter of an amorphous porous material; and calculating an acoustic physical property value of the amorphous porous material from the analyzed parameter. The parameter includes one or more selected from the group consisting of an average pore radius ($\overline{R}_p$), an average pore throat radius ($\overline{R}_t$), an average bonding angle ($\overline{\theta}_{p-p}$) between neighboring pores, and a porous material skeleton thickness ($T_f$), and the acoustic physical property value includes one or more selected from a group consisting of a porosity ($\phi$), a tortuosity ($\alpha_\infty$), a flow resistivity ($\sigma$), a thermal characteristic length ($\Lambda'$), and a viscous characteristic length ($\Lambda$).

The method may further include predicting an absorption coefficient from the acoustic physical property value.

The obtaining of the parameter of the amorphous porous material may include obtaining the amorphous porous material from a pre-shaped product, obtaining a three-dimensional pore connection structure of the amorphous porous material by photographing a tomographic image of the amorphous porous material, and obtaining the parameter from the three-dimensional pore connection structure of the amorphous porous material.

The average pore radius ($\overline{R}_p$) may be obtained by calculating using Equation 1 below, $$\overline{R}_p = \frac{\int R_p \cdot f(R_p) \cdot V_p dR_p}{\int f(R_p) \cdot V_p dR_p}. \qquad \text{Equation 1}$$

In Equation 1, the $R_P$ refers to a pore radius, and the $V_P$ refers to a pore volume.

The average pore throat radius ($\overline{R}_t$) may be obtained by calculating using Equation 2 below, $$\overline{R}_t = \frac{\int R_t \cdot g(R_t) \cdot S_t dR_t}{\int g(R_t) \cdot S_t dR_t}. \qquad \text{Equation 2}$$

In Equation 2, the $R_t$ refers to a pore throat radius, and the $S_t$ refers to a pore throat area.

The average bonding angle ($\overline{\theta}_{p-p}$) between the neighboring pores may be a value obtained by arithmetic averaging a frequency distribution value for each angle with the angle of 5 degrees as a basic indicator for a bonding angle ($\theta_{i'j'}$) between the neighboring pores calculated by Equation 3 below, $$\theta_{i'j'} = \arccos\left(\frac{z_{i'} - z_{j'}}{L_{i'j'}}\right). \qquad \text{Equation 3}$$

In Equation 3, the $z_{i'}$ and the $z_{j'}$ refer to z directional coordinate values of the neighboring i'th and j'th pores on the shortest path, and the $L_{i'j'}$ refers to a distance between the neighboring pores.

The porous material skeleton thickness ($T_f$) may be obtained by calculating using Equation 4 below, $$T_f = \frac{2 \times r_v \times \sum I}{N_{v,surf}}.$$ Equation 4

In Equation 4, the $r_v$ refers to a resolution value of the tomographic image, the $\Sigma I$ refers to a value obtained by adding all surface distance map values, and the $N_{v,surf}$ refers to the number of voxels corresponding to the surface.

The porosity ($\phi$) may be obtained by calculating using Equation 5 below, $$\phi = \frac{V_{fluid}}{V_{fluid} + V_{solid}}$$ Equation 5

In Equation 5, the $V_{fluid}$ may be a value calculated by Equation 6 below, and the $V_{solid}$ is a value calculated by Equation 7 below, $$V_{fluid} = \frac{4\pi}{3} \overline{R}_p^3 \times N_p.$$ Equation 6

In Equation 6, the $\overline{R}_P$ refers to the average pore radius, and the $N_p$ refers to the number of pores, $$V_{solid} = S_{solid} \times \overline{T}_f$$ Equation 7

In Equation 7, the $S_{solid}$ may be obtained by calculating using Equation 8 below, and the $\overline{T}_f$ refers to the porous material skeleton thickness, $$S_{solid} = 4\pi \overline{R}_p^2 - \pi \left\{ \overline{R}_t^2 + \left( \overline{R}_p - \sqrt{\overline{R}_p^2 - \overline{R}_t^2} \right) \right\} \times \overline{C}_n$$ Equation 8

In Equation 8, the $\overline{R}_p$ refers to the average pore radius, the $\overline{R}_t$ refers to the average pore throat radius, and the $\overline{C}_n$ refers to the average pore coordination number.

The tortuosity ($\alpha_\infty$) may be obtained by calculating using Equation 9 below, $$\alpha_\infty = \left( \frac{1}{\cos \overline{\theta}_{p-p}} \right)^2$$ Equation 9

In Equation 9, the $\overline{\theta}_{p-p}$ refers to an average bonding angle between the neighboring pores.

The flow resistivity ($\sigma$) may be obtained by calculating using Equation 10 below, $$\sigma = \frac{8\mu\alpha_\infty}{R_0^2 \phi} \left[ \frac{2 + 3(\delta/R_0)^2}{2\{1 - (\delta - R_0)^2\}^{3.5}} \right] \times \left[ 1 + \frac{16\pi^2}{3} \left( \frac{\delta}{\overline{L}_{p-p}} \right)^2 \frac{1 - (\delta/R_0)^2}{2 + 3(\delta/R_0)^2} \right].$$ Equation 10

In Equation 10, the $\mu$ refers to the viscosity of fluid (air), the $\alpha_\infty$ refers to the tortuosity, the $\phi$ refers to the porosity, the $\overline{L}_{p-p}$ refers to the average distance between the neighboring pores, the $R_0$ may be obtained by calculating using Equation 11 below, and the $\delta$ may be obtained by calculating using Equation 12 below, $$R_0 = (\overline{R}_p + \overline{R}_t)/2$$ Equation 11

In Equation 11, the $\overline{R}_p$ refers to the average pore radius, and the $\overline{R}_t$ refers to the average pore throat radius, $$\delta = (\overline{R}_p - \overline{R}_t)/2$$ Equation 12

In Equation 12, the $\overline{R}_p$ refers to the average pore radius, and the $\overline{R}_t$ refers to the average pore throat radius.

The thermal characteristic length ($\Lambda'$) may be obtained by calculating using Equation 13 below, $$\Lambda' = 2 \frac{\frac{4\pi}{3} \overline{R}_p^3}{4\pi \overline{R}_p^2 - \pi \overline{R}_t^2 \times \overline{C}_n}.$$ Equation 13

In Equation 13, the $\overline{R}_p$ refers to the average pore radius, the $\overline{R}_t$ refers to the average pore throat radius, and the en refers to the average pore coordination number.

The viscous characteristic length ($\Lambda'$) may be obtained by calculating using Equation 14 below, $$\Lambda \cong \Lambda' \cdot m(\phi) = \Lambda' \left( \frac{\phi}{26(1-\phi)} \right)^2.$$ Equation 14

In Equation 14, the $\Lambda'$ refers to the thermal characteristic length, and the $\phi$ refers to the porosity.

The method for predicting the physical properties of the amorphous porous material according to various exemplary embodiments of the present invention may estimate the acoustic characteristics with the amorphous porous material which is an amorphous specimen even without separately producing the formalized specimen such as the cylindrical specimen or the flat specimen. Accordingly, it is possible to estimate the acoustic physical properties of the porous material of the pre-shaped component or the porous material of the competitor's component, and finally, to mutually compare the absorption coefficients. Further, since the method for predicting the physical properties of the amorphous porous material according to various exemplary embodiments of the present invention may estimate the acoustic physical properties through the analysis of the three-dimensional pore connection structure, which is a microstructure of the amorphous specimen even without acoustic impedance, thereby estimating the acoustic physical properties which accurately reflect the characteristics of the actual specimen. Further, it is also possible to propose the appropriate microstructure change method when changing the absorption characteristics of the urethane foam.

The present methods also may suitably include use of a controller or controller unit to assist or carry out the steps. For instance, in certain aspects, a method for predicting physical properties of an amorphous porous material may include obtaining (optionally by or with use of a controller) a parameter of an amorphous porous material; and calculating by or with use of a controller an acoustic physical property value of the amorphous porous material from the analyzed parameter. The parameter includes one or more selected from the group consisting of an average pore radius ($\overline{R}_p$), an average pore throat radius ($\overline{R}_t$), an average bonding angle ($\overline{\theta}_{p-p}$) between neighboring pores, and a porous material skeleton thickness ($T_f$), and the acoustic physical property value includes one or more selected from a group consisting of a porosity ($\phi$), a tortuosity ($\alpha_\infty$), a flow resistivity ($\sigma$), a thermal characteristic length ($\Lambda'$), and a viscous characteristic length ($\Lambda$). The method may further include predicting by or with use of a controller) an absorption coefficient from the acoustic physical property value. In certain aspects, at least one step (and preferably at least two steps) of obtaining, calculating or predicting includes use of a controller to carry out the step.

The present methods are a significant advancement and can provide substantial advantages. Thus, for instance, an amorphous porous material that is proposed for use may be evaluated for acoustic physical properties at an early stage before implementing into a larger systems such as a vehicle, thereby providing significant cost and time savings.

The effects of the present invention are not limited to the aforementioned effects. It should be understood that the effects of the present invention include all effects which may be inferred from the following description.

The above and other features of the invention are discussed infra.

BRIEF DESCRIPTION OF THE DRAWINGS

The above and other features of the present invention will now be described in detail with reference to certain exemplary Examples thereof illustrated in the accompanying drawings which are given herein below by way of illustration only, and thus are not limitative of the present invention, and wherein.

Figure 1:
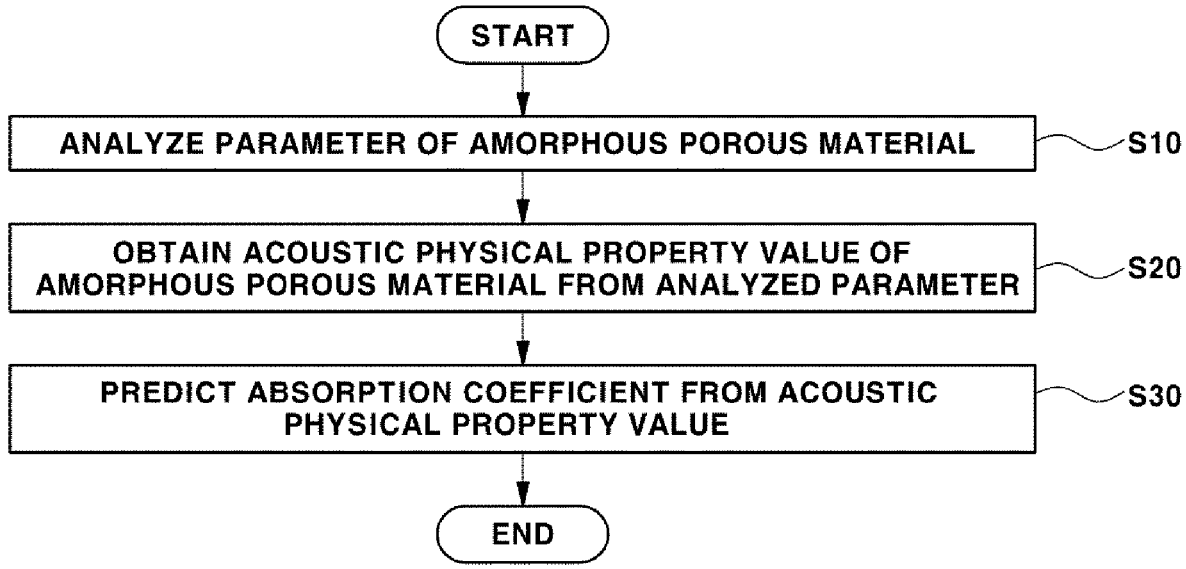
FIG. 1 shows an exemplary method for predicting physical properties of an amorphous porous material according to an exemplary embodiment of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, positions, and shapes will be determined in section by the particular intended application and use environment.

In the figures, reference numbers refer to the same or equivalent sections of the present invention throughout the several figures of the drawing.

DETAILED DESCRIPTION

As described above, objects, other objects, features, and advantages according to various exemplary embodiments of the present invention will be readily understood through the following preferred Examples associated with the accompanying drawings. However, the present invention is not limited to the Examples described herein and may also be embodied in other forms. Rather, the Examples introduced herein are provided so that the invention may be made thorough and complete, and the spirit according to various exemplary embodiments of the present invention may be sufficiently conveyed to those skilled in the art.

Similar reference numerals are used for similar components while describing each drawing. In the accompanying drawings, the dimensions of the structures are illustrated to be enlarged than the actual one for clarity of the present invention.

In this specification, it should be understood that terms such as "comprise" or "have" are intended to indicate that there is a feature, a number, a step, an operation, a component, a part, or a combination thereof described on the specification, and do not exclude the possibility of the presence or the addition of one or more other features, numbers, steps, operations, components, parts, or combinations thereof in advance.

Further, if a numerical range is disclosed herein, such a range is continuous, and includes unless otherwise indicated, every value from the minimum value to and including the maximum value of such a range. Furthermore, if such a range refers to integers, unless otherwise indicated, every integer from the minimum value to and including the maximum value is included.

In the present specification, if a range is described for a variable, it will be understood that the variable includes all values within the described range including the described endpoints of the range. For example, it will be understood that a range of "5 to 10" includes not only values of 5, 6, 7, 8, 9, and 10 but also any sub-range such as 6 to 10, 7 to 10, 6 to 9, and 7 to 9, and also includes any value between reasonable integers within the scope of the described ranges such as 5.5, 6.5, 7.5, 5.5 to 8.5, 6.5 to 9, and the like. Further, it will be understood that a range of "10% to 30%" includes, for example, not only all integers including values, such as 10%, 11%, 12%, and 13%, and 30% but also any sub-range such as 10% to 15%, 12% to 18%, and 20% to 30%, and also includes any value between reasonable integers within the scope of the described range, such as 10.5%, 15.5%, and 25.5%. Unless otherwise indicated, all numbers, values, and/or expressions referring to quantities of ingredients, reaction conditions, polymer compositions, and formulations used herein are to be understood as modified in all instances by the term "about" as such numbers are inherently approximations that are reflective of, among other things, the various uncertainties of measurement encountered in obtaining such values.

Further, unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicles in general such as passenger automobiles including sports utility vehicles (operation SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles. It is understood that the term controller/control unit refers to a hardware device that includes a memory and a processor. The memory is configured to store modules or program instructions and the processor is specifically programmed to execute the program instructions or operate the modules to perform one or more processes which are described herein.

In an aspect, provided is a method for predicting physical properties of an amorphous porous material. The method may include obtaining a porous material from a pre-shaped product or the like, obtaining a three-dimensional pore connection structure because the porous material may be photographed as a tomographic image, and accordingly, obtaining parameters and an acoustic physical property value, unlike the conventional method for measuring physical properties by separately producing the formalized specimen such as the cylindrical specimen or flat specimen. The amorphous porous material may be one or more materials selected from the group consisting of a material, for example, urethane foam, polyimide foam, and melamine foam, which may be obtained by the general method from the pre-shaped product or the like, and is not limited to a specific material.

FIG. 1 shows a flowchart illustrating a method for predicting physical properties of an amorphous porous material according to an exemplary embodiment of the present invention. As shown in FIG. 1, the method may include obtaining parameters of an amorphous porous material (S10), obtaining acoustic physical property values of the amorphous porous material from the analyzed parameters (S20), and predicting an absorption coefficient from the acoustic physical property values S30).

Figure 2:
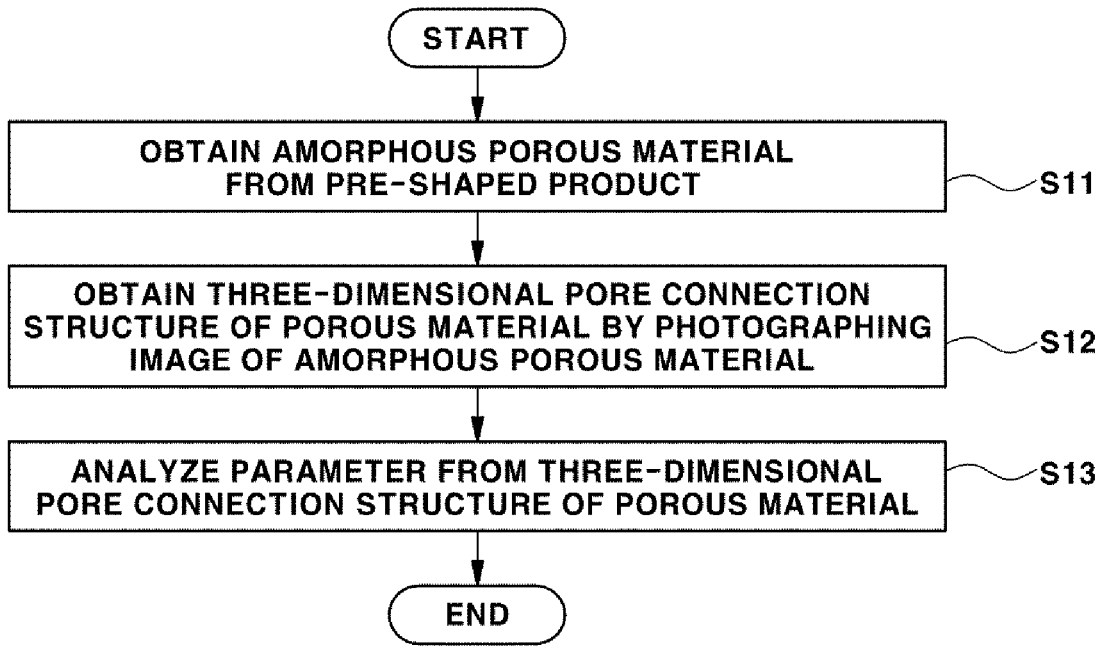
FIG. 2 shows an exemplary step of analyzing parameters of the amorphous porous material according to an exemplary embodiment of the present invention.

As shown in the flowchart shown in FIG. 2, the analyzing of the parameters of the amorphous porous material (S10) includes obtaining an amorphous porous material from a pre-shaped product (S11); obtaining a three-dimensional pore connection structure of the porous material by taking a tomographic image of the amorphous porous material (S12); and obtaining parameters from the three-dimensional pore connection structure of the porous material (S13).

The obtaining of the amorphous porous material (S11) is a step of obtaining the porous material from the pre-shaped product which has been already manufactured. The obtaining of the porous material may obtain the porous material by a general method which is known in the technical field related to the present invention. The amorphous porous material may be about 4 to 30 mm in size. When the size is less than 4 mm, there is a disadvantage in that the number of sample pores is small, such that reliability may be degraded when calculating the average value, and when the size is greater than about 30 mm, there is a disadvantage in that the number of sample pores is large, such that it takes too much time to analyze a micro-CT image in S12 below. That is, since this step may omit separately producing the formalized specimen such as the cylindrical specimen or the flat specimen unlike the conventional method for predicting physical properties, it is possible to measure the physical properties efficiently and economically.

Figure 3A:
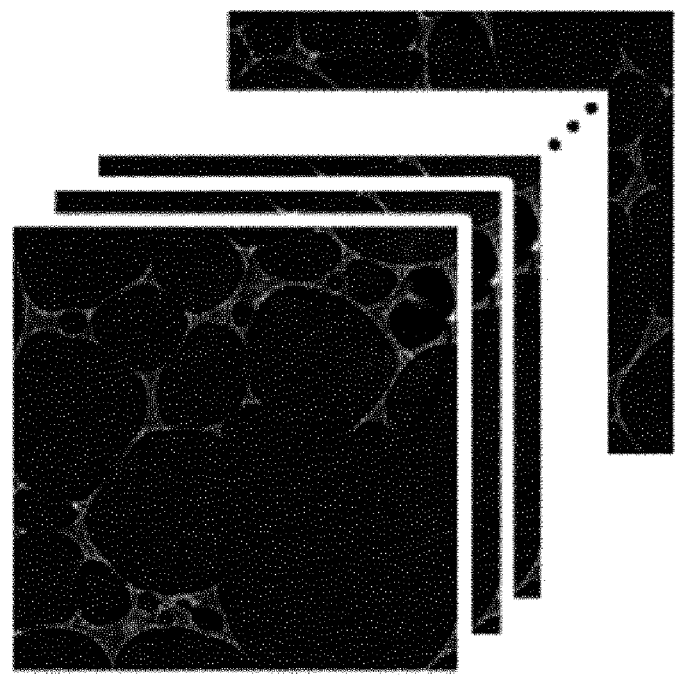
FIG. 3A shows a series of tomographic images of an amorphous porous material photographed by using a micro-CT according to an exemplary embodiment of the present invention.
Figure 3B:
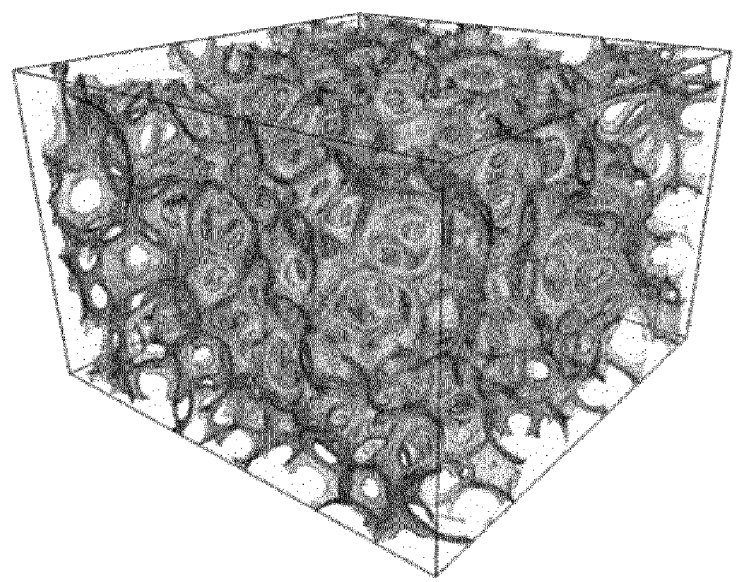
FIG. 3B is a diagram illustrating a three-dimensional structure image of the amorphous porous material which is obtained by laminating the tomographic images photographed in FIG. 3A according to an exemplary embodiment of the present invention.
Figure 3C:
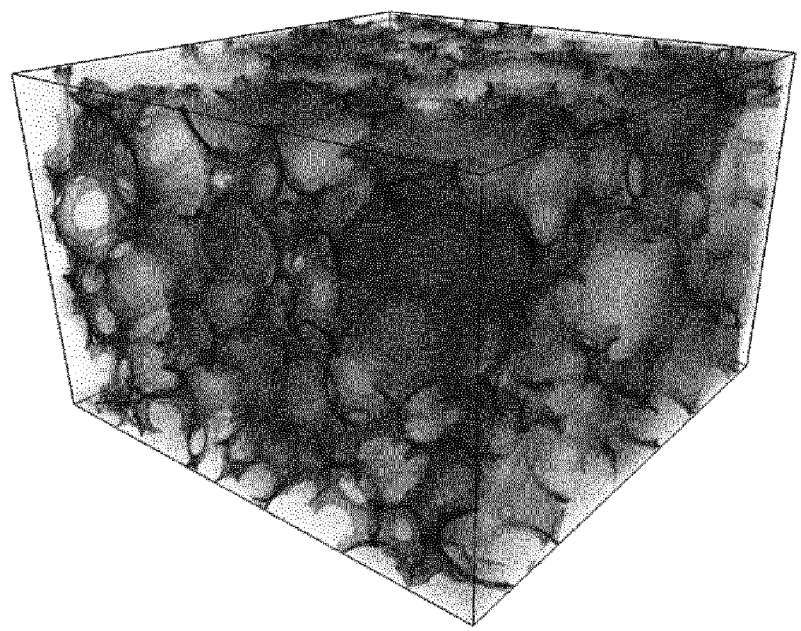
FIG. 3C is a diagram illustrating an image which is obtained by fractionating pores having a spherical shape from the three-dimensional structure of the amorphous porous material which is derived in FIG. 3B according to an exemplary embodiment of the present invention.
Figure 3D:
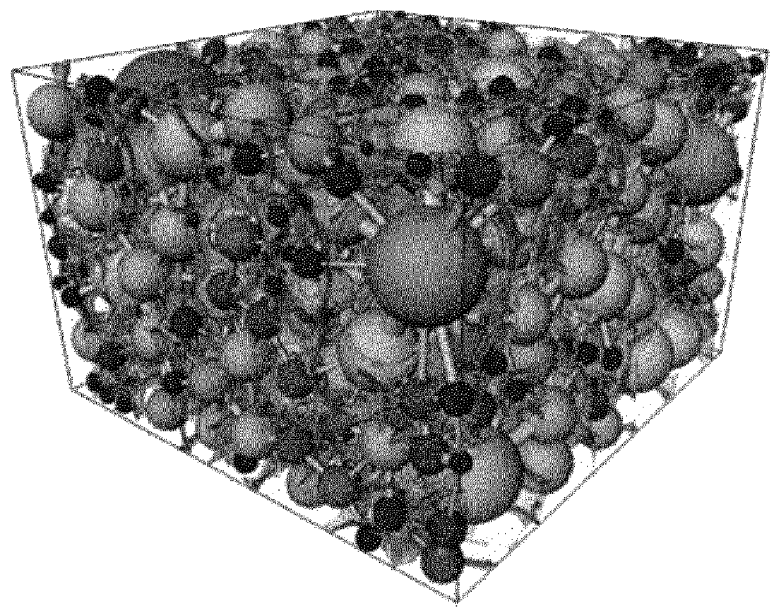
FIG. 3D is a diagram illustrating an image representing a three-dimensional pore connection structure of the amorphous porous material from the pores which are fractionated in FIG. 3C according to an exemplary embodiment of the present invention.

The obtaining of the three-dimensional pore connection structure of the amorphous porous material (S12) is a step of obtaining the three-dimensional pore connection structure of the amorphous porous material by taking the tomographic image of the amorphous porous material. FIG. 3A shows a diagram illustrating a series of tomographic images of an amorphous porous material photographed by using a micro-CT. As shown in FIG. 3A, the tomographic image of the porous material obtained from the pre-shaped product may be photographed at an interval of about 0.95 μm (imaging resolution) in the thickness direction of the porous material by using the micro-CT. Next, as shown in FIG. 3B, after the photographed tomography images are laminated, the shape of the skeleton may be determined, and the three-dimensional structure of the amorphous porous material may be obtained through a distance transform (a method for expressing as the shortest distance from a pixel in an object to a background). As shown in FIG. 3C, by separately fractioning spherical pores from the obtained three-dimensional structure of the amorphous porous material by using a Watershed algorithm (a technique of splitting the overlapped section into an area which is surrounded without overflowing each other), it is possible to eventually obtain the three-dimensional pore connection structure of the amorphous porous material, as shown in FIG. 3D.

The analyzing of the parameters (S13) is a step of obtaining the parameters from the three-dimensional pore connection structure of the amorphous porous material. This step is an essential step for predicting the physical properties of the present invention with important parameters for later predicting a porosity ($\phi$), a tortuosity ($\alpha_\infty$), a flow resistivity ($\sigma$), a thermal characteristic length ($\Lambda'$), and a viscous characteristic length ($\Lambda$), which are acoustic physical property values, and an absorption coefficient through these.

The parameters of the amorphous porous material according to an exemplary embodiment of the present invention may include one or more selected from the group consisting of an average pore radius ($\overline{R}_P$), an average pore throat radius ($\overline{R}_t$), an average bonding angle ($\overline{\theta}_{p\text{-}p}$) between neighboring pores, and a porous material skeleton thickness ($\overline{T}_f$).

Figure 4:
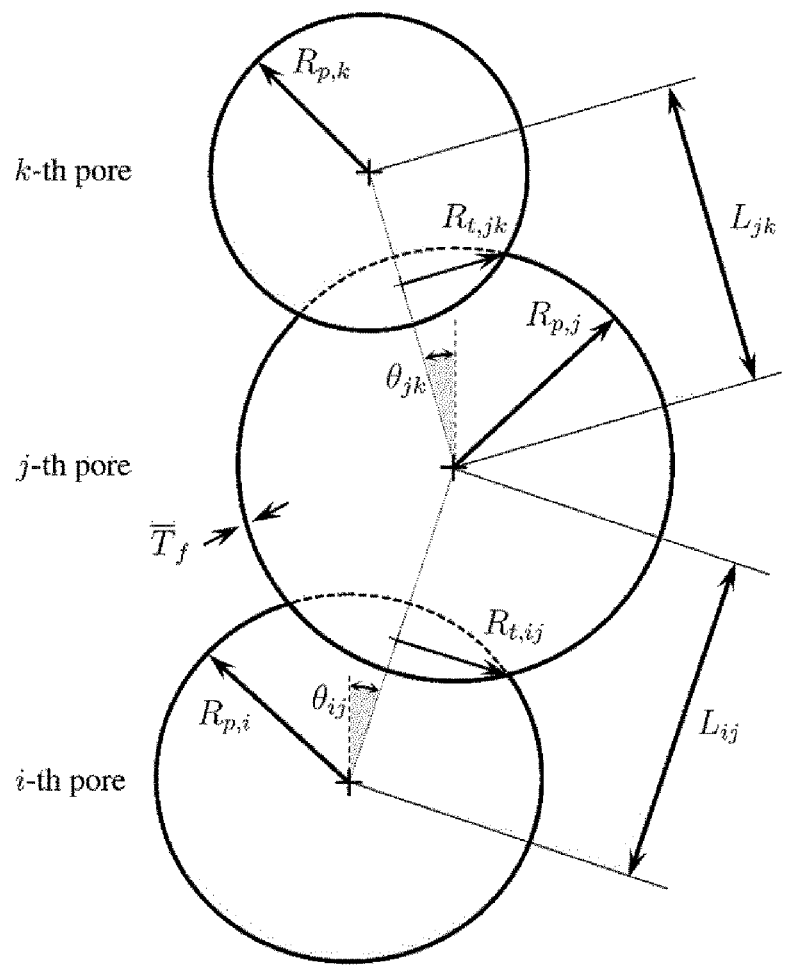
FIG. 4 is a cross-sectional diagram of any three neighboring pores ($^i$-pore, $^j$-pore, and $^k$-pore) within the three-dimensional pore connection structure of the amorphous porous material according to an exemplary embodiment of the present invention.

FIG. 4 illustrates a cross-sectional diagram of any three neighboring pores ($i$-pore, $j$-pore, and $k$-pore) within the three-dimensional pore connection structure of the amorphous porous material. As shown in FIG. 4, the $R_P$ refers to a pore radius, the $R_t$ refers to a pore throat radius ($R_{t,ij}$ is a half of a common chord of the $i$-pore and the $j$-pore), the $L_{ij}$ refers to a distance between the neighboring pores (distance between the $i$-pore and the $j$-pore), and the $\theta_{ij}$ refers to a bonding angle between the neighboring pores (bonding angle between the $i$-pore and the $j$-pore). Each parameter will be described below with reference to the above.

The average pore radius ($\overline{R}_p$) is a representative value of the radii of all distributed pores which are included in the three-dimensional pore connection structure of the amorphous porous material. There may occur a disadvantage in that the arithmetic average processing of the radii of the all distributed pores which are included in the three-dimensional pore connection structure does not reflect the fluid-acoustic characteristics of the pore. Accordingly, the average pore radius ($\overline{R}_p$) according to an exemplary embodiment of the present invention may be predicted from a volume added average as a representative value in order to reflect a volume specific gravity for each pore. Particularly, the average pore radius ($\overline{R}_p$) may be calculated by Equation 1 below.

$$\overline{R}_p = \frac{\int R_p \cdot f(R_p) \cdot V_p dR_p}{\int f(R_p) \cdot V_p dR_p} \qquad \text{Equation 1}$$

In Equation 1, the $R_P$ refers to the pore radius, and the $V_p$ refers to the pore volume.

The average pore throat radius ($\overline{R}_p$) refers to a representative value of the radii of all distributed pore throats which are included in the three-dimensional pore connection structure of the amorphous porous material. There may occur a disadvantage in that the arithmetic average processing of the radii of all distributed pore throats which are included in the three-dimensional pore connection structure does not reflect the fluid-acoustic characteristics of the pore. Accordingly, the average pore throat radius ($\overline{R}_t$) of the present invention may be predicted from the area added average as a representative value in order to reflect the area specific gravity for each pore throat. Particularly, the average pore throat radius ($\overline{R}_t$) may be calculated by Equation 2 below.

$$\overline{R}_t = \frac{\int R_t \cdot g(R_t) \cdot S_t dR_t}{\int g(R_t) \cdot S_t dR_t} \qquad \text{Equation 2}$$

In Equation 2, the $R_t$ refers to the pore throat radius, and the $S_t$ refers to a pore throat area.

Figure 5:
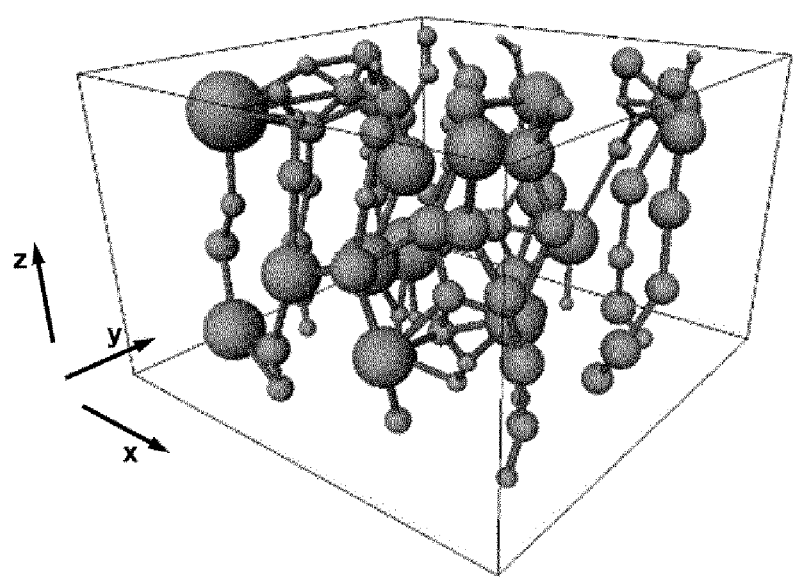
FIG. 5 shows an image representing the shortest path between pores, which exist at an inlet and an outlet on a fluid moving path, derived by using a Dijkstra's algorithm according to an exemplary embodiment of the present invention.

The average bonding angle ($\overline{\theta}_{p\text{-}p}$) between the neighboring pores is a representative value of the bonding angles of all distributed pores which are included in the three-dimensional pore connection structure of the amorphous porous material. Since the internal pores included in the amorphous porous material are distributed at arbitrary positions, there is a high possibility that the arithmetic averaged value converges to zero to become meaningless data if the internal pores are simply arithmetic averaged. Accordingly, as shown in FIG. 5, in order to obtain the average bonding angle ($\bar{\theta}_{p-p}$) between the neighboring pores according to an exemplary embodiment of the present invention, the shortest path between the pores which exist at the inlet and the outlet on the fluid moving path may be derived by using a Dijkstra's algorithm. Next, the average bonding angle ($\bar{\theta}_{p-p}$) between the neighboring pores may be obtained by deriving the bonding angle ($\theta_{i'j'}$) between the neighboring pores from the derived shortest path by the calculation of Equation 3 below, and then arithmetic averaging a frequency distribution value for each angle with the angle of 5 degrees as a basic indicator.

$$\theta_{i'j'} = \arccos\left(\frac{z'_i - z'_j}{L_{i'j'}}\right) \qquad \text{Equation 3}$$

In Equation 3, the $z_{i'}$ and the $z_{j'}$ refer to z directional coordinate values of the z direction of the neighboring i'th and j'th pores on the shortest path, and the $L_{i'j'}$ refers to a distance between the neighboring pores.

The porous material skeleton thickness ($\bar{T}_f$) is a representative value of the thickness of the skeleton which forms the pore. Since the thickness of the internal pore skeleton included in the amorphous porous material is composed of various shapes and thicknesses, it is difficult to calculate the internal pore skeleton thickness with the simple average value. Accordingly, the present invention may calculate the porous material skeleton thickness ($\bar{T}_f$) by Equation 4 below by using image element parameters such as micro-CT imaging resolution and voxels.

$$\bar{T}_f = \frac{2 \times r_v \times \sum I}{N_{v,surf}} \qquad \text{Equation 4}$$

Figure 6:
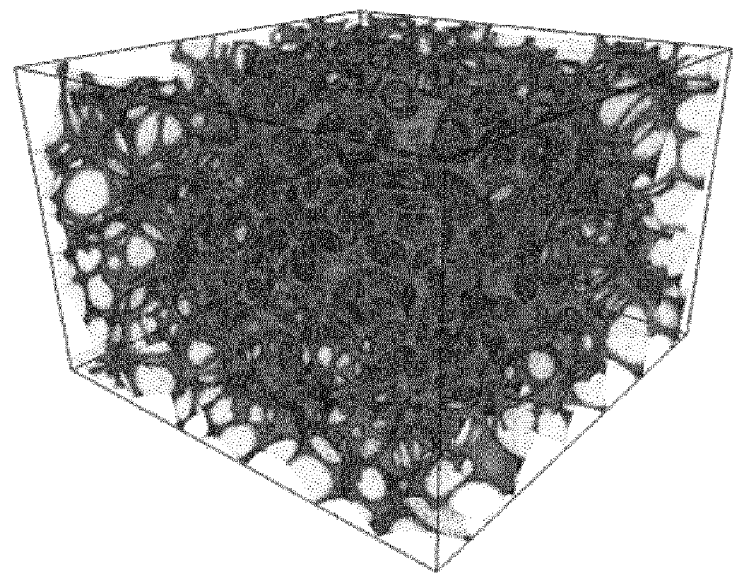
FIG. 6 shows a surface distance map according to an exemplary embodiment of the present invention.

In Equation 4, the $r_v$ refers to a resolution value of the tomographic image, the $\Sigma I$ refers to a value obtained by adding all surface distance map values, and the $N_{v,surf}$ refers to the number of voxels which corresponds to the porous material skeleton surface. The distance map refers to the shortest distance from the current voxel position to the voxel at the interface between the skeleton and the pore, as shown in FIG. 6.

The obtaining of the acoustic physical property values of the porous material (S20) is a step of obtaining the acoustic physical property values of the amorphous porous material from the analyzed parameters. The acoustic physical property values may include one or more selected from the group consisting of a porosity ($\phi$), a tortuosity ($\alpha_\infty$), a flow resistivity ($\sigma$), a thermal characteristic length ($\Lambda'$), and a viscous characteristic length ($\Lambda$).

The porosity ($\phi$) refers to a ratio of the volume occupied by the fluid phase of the total volume of the amorphous porous material. Conventionally, there is a technique of measuring the porosity using argon gas, but there is no prediction method. Accordingly, provided is a method for predicting the porosity based on the parameters obtained through the three-dimensional pore connection structure. Particularly, the porosity ($\phi$) may be calculated by Equation 5 below.

$$\phi = \frac{V_{fluid}}{V_{fluid} + V_{solid}} \qquad \text{Equation 5}$$

In Equation 5, the pore volume ($V_{fluid}$) may be calculated by Equation 6 below. For example, it is assumed that the fractionated pores have a complete sphere shape.

$$V_{fluid} = \frac{4\pi}{3}\bar{R}_p^3 \times N_p \qquad \text{Equation 6}$$

In Equation 6, the $\bar{R}_P$ refers to an average pore radius, and the $N_P$ refers to the number of pores.

In Equation 5, the skeleton volume ($V_{solid}$) refers to a value calculated by Equation 7 below. That is, the skeleton volume ($V_{solid}$) may be predicted by multiplying the surface area ($S_{solid}$) of the skeleton by the thickness of the porous material skeleton.

$$V_{solid} = S_{solid} \times \bar{T}_f \qquad \text{Equation 7}$$

In Equation 7, the $S_{solid}$ is calculated by Equation 8 below, and the $\bar{T}_f$ refers to the thickness of the porous material skeleton.

$$S_{solid} = 4\pi \bar{R}_p^2 - \pi\left\{\bar{R}_t^2 + \left(\bar{R}_p - \sqrt{\bar{R}_p^2 - \bar{R}_t^2}\right)\right\} \times \bar{C}_n \qquad \text{Equation 8}$$

In Equation 8, the $\bar{R}_p$ refers to an average pore radius, the $\bar{R}_t$ refers to an average pore throat radius, and the $\bar{C}_n$ refers to an average pore coordination number. The average pore coordination number may be calculated by averaging the number of pore throats connected to one pore in the three-dimensional pore connection structure shown in FIG. 3D.

Figure 7:
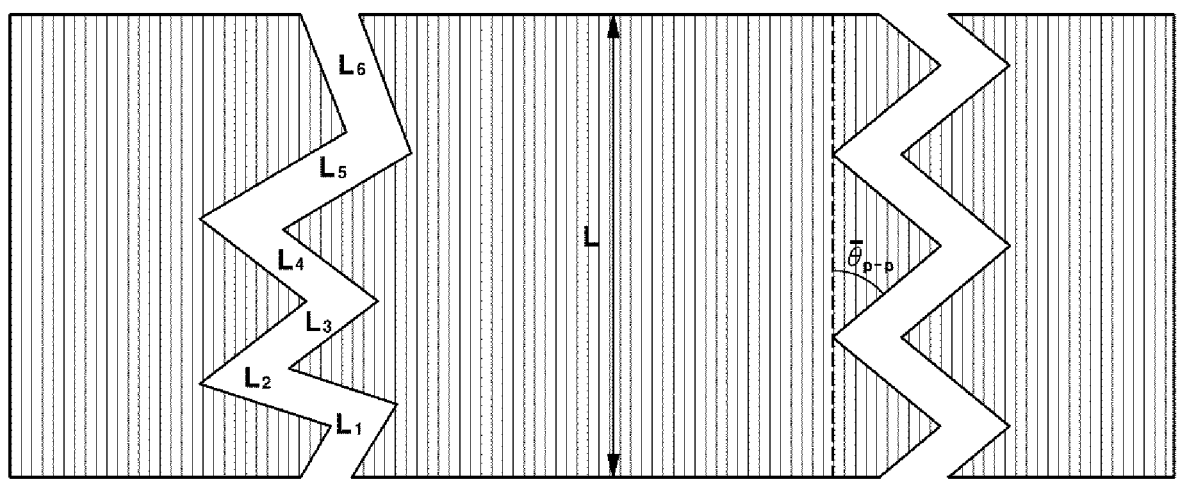
FIG. 7 shows an image representing an inner tortuosity of the amorphous porous material in order to obtain a tortuosity according to an exemplary embodiment the present invention.

The tortuosity ($\alpha_\infty$) refers to the complexity of the fluid phase and solid phase formation structure inside the amorphous porous material. The tortuosity ($\alpha_\infty$) is the square of the ratio of the material thickness and the acoustic actual effective moving distance, and as shown in FIG. 7, is expressed by Equation 15 below.

$$\alpha_\infty = \left(\frac{L_{eff}}{L}\right)^2 \qquad \text{Equation 15}$$

In Equation 15, $L_{eff} = L_1 + L_2 + \ldots + L_n$, and the L refers to the thickness of the amorphous porous material.

Conventionally, there is a technique of measuring the tortuosity using an ultrasonic sensor, but the specimen having a cylindrical shape is separately required, and there is no prediction method. Accordingly, the present invention provides a method for predicting the porosity based on the parameters which are obtained through the three-dimensional pore connection structure.

Particularly, the tortuosity ($\alpha_\infty$) may be calculated by Equation 9 below.

$$\alpha_\infty = \left(\frac{1}{\cos\overline{\theta}_{p-p}}\right)^2 \qquad \text{Equation 9}$$

In Equation 9, the $\overline{\theta}_{p-p}$ refers to the average bonding angle between neighboring pores.

The flow resistivity ($\sigma$) means the pressure drop due to the viscosity of the flow which crosses the interior of the porous material. Conventionally, there is a technique of measuring the flow resistivity using the pressure sensor, but there is a problem in that the specimen having a cylindrical shape is separately required. Further, the flow inside the amorphous porous material may be conventionally modeled in the form of a circular cylinder, but this has a problem in that the properties of the pore and the pore throat are not reflected at all. Accordingly, provided is a method for predicting the flow resistivity based on the parameters obtained through the three-dimensional pore connection structure.

Figure 8:
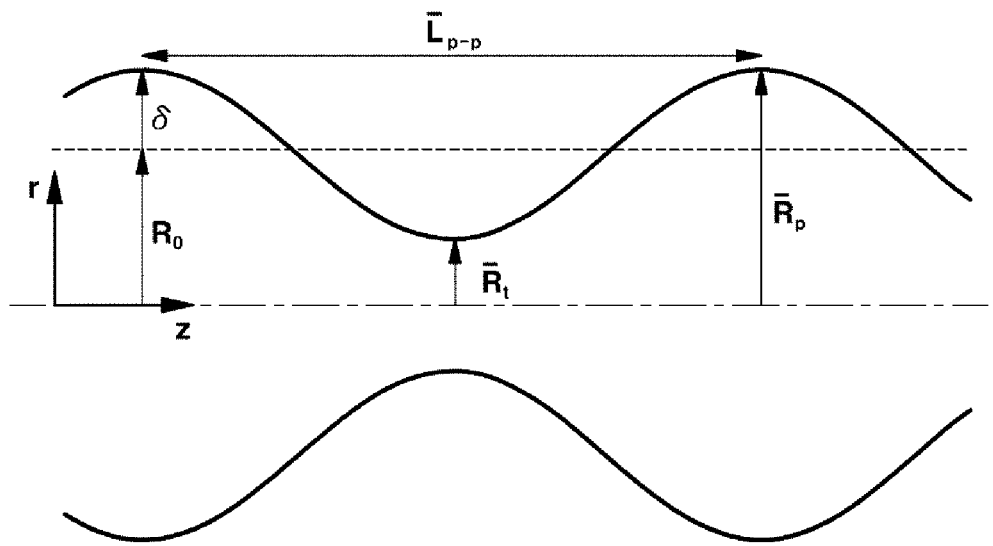
FIG. 8 shows an exemplary modeling, by a differentiable function, the continuous shape of the pores and the pore throats inside the amorphous porous material based on the three-dimensional pore connection structure according to an exemplary embodiment of the present invention.

Particularly, as shown in FIG. 8, the continuous shape of the pores and the pore throats inside the amorphous porous material may be modeled by a differentiable function based on the three-dimensional pore connection structure, as expressed by Equation 16 below.

$$r(z) = R_0\left[1 + \frac{\delta}{R_0}\sin\left(\frac{2\pi z}{\overline{L}_{p-p}}\right)\right] \qquad \text{Equation 16}$$

In Equation 16, the $\overline{L}_{p-p}$ refers to an average distance between the neighboring pores, a median value ($R_0$) of the radii of the pore and the pore throat is calculated by Equation 11 below, and the amplitude ($\delta$) is calculated by Equation 12 below.

$$R_0 = (\overline{R}_p + \overline{R}_t)/2 \qquad \text{Equation 11}$$

In Equation 11, the $\overline{R}_p$ refers to the average pore radius, and the $\overline{R}_t$ refers to the average pore throat radius.

$$\delta = (\overline{R}_p - \overline{R}_t)/2 \qquad \text{Equation 12}$$

In Equation 12, the $\overline{R}_p$ refers to the average pore radius, and the $\overline{R}_t$ refers to the average pore throat radius.

Based on the differentiable function (Equation 16) modeling the continuous form of the pores and the pore throats, the flow resistivity ($\sigma$) may calculate the pressure drop of the flow which passes through the pores and the pore throats by Equation 10 below. Particularly, the first term $$\left(\frac{\delta\mu\alpha_\infty}{R_0^2\phi}\right)$$

in Equation 10 below means the flow resistivity of the flow through a cylindrical tube with a radius ($R_0$), the second term $$\left(\frac{2 + 3(\delta/R_0)^2}{2(1 - (\delta/R_0)^2)^{3.5}}\right)$$

below means the influence by the amplitude ($\delta$), and the third term $$\left(1 + \frac{16\pi^2}{3}\left(\frac{\delta}{\overline{L}_{p-p}}\right)^2\frac{1-(\delta/R_0)^2}{2+3(\delta/R_0)^2}\right)$$

means the influence by the ($\overline{L}_{p-p}$) between the pores.

$$\sigma = \frac{8\mu\alpha_\infty}{R_0^2\phi}\left[\frac{2+3(\delta/R_0)^2}{2((1-\delta/R_0)^2)^{3.5}}\right] \times \left[1 + \frac{16\pi^2}{3}\left(\frac{\delta}{\overline{L}_{p-p}}\right)^2\frac{1-(\delta/R_0)^2}{2+3(\delta/R_0)^2}\right] \qquad \text{Equation 10}$$

In Equation 10, the $\mu$ refers to the viscosity of the fluid (air), the $\alpha_\infty$ refers to the tortuosity, the $\phi$ refers to the porosity, the $\overline{L}_{p-p}$ refers to the average distance between the neighboring pores, the $R_0$ is calculated by Equation 11, and the $\delta$ is calculated by Equation 12.

Figure 9:
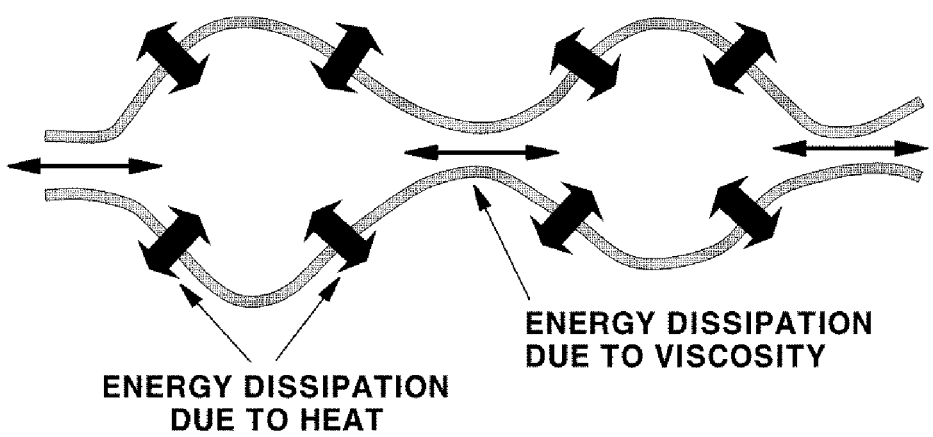
FIG. 9 shows an energy dissipation effect due to heat and viscosity at the inner interface of the amorphous porous material according to an exemplary embodiment of the present invention.

As shown in FIG. 9, the thermal characteristic length ($\Lambda'$) and the viscous characteristic length ($\Lambda$) mean the energy dissipation effect due to heat and viscosity at the inner interface of the amorphous porous material, respectively.

An equation of defining the thermal characteristic length ($\Lambda'$) is expressed by Equation 17 below.

$$\Lambda' = 2\frac{\int_V dV}{\int_A dA} = \frac{V_{fluid}}{A_{solid}} \qquad \text{Equation 17}$$

In Equation 17, the $V_{fluid}$ refers to the pore volume, and the $A_{solid}$ refers to the surface area of the solid phase.

Further, an equation of defining the viscous characteristic length ($\Lambda$) is expressed by Equation 18 below.

$$\Lambda = 2\frac{\int_V v^2(r)dV}{\int_A v^2(r_s)dA} \qquad \text{Equation 18}$$

In Equation 18, the $v(r)$ refers to the fluid velocity inside the pore, the $v(r_s)$ refers to the fluid velocity of the pore surface, the V refers to the volume of the pore, and the A refers to the surface area of the contact surface between the pore and the skeleton.

Conventionally, there is an inverse analysis technique of the thermal and viscous characteristic lengths, but there is a problem in that all acoustic physical property data as well as the absorption coefficient are required to exist. Accordingly, provided is a method for predicting the thermal characteristic length ($\Lambda'$) and the viscous characteristic length ($\Lambda$) based on the parameters obtained through the three-dimensional pore connection structure and the porosity obtained therefrom.

Particularly, the thermal characteristic length ($\Lambda'$) is calculated by Equation 13 below.

$$\Lambda' = 2\frac{\frac{4\pi}{3}\overline{R}_p^3}{4\pi\overline{R}_p^2 - \pi\overline{R}_t^2 \times \overline{C}_n} \qquad \text{Equation 13}$$

In Equation 13, the $\overline{R}_p$ refers to the average pore radius, the $\overline{R}_t$ refers to the average pore throat radius, and the $\overline{C}_n$ refers to the average pore coordination number.

Further, the viscous characteristic length (Λ) is calculated by Equation 14 below.

$$\Lambda \cong \Lambda' \cdot m(\phi) = \Lambda'\left(\frac{\phi}{26(1-\phi)}\right)^2 \quad \text{Equation 14}$$

In Equation 14, the Λ' refers to the thermal characteristic length, and the ϕ refers to the porosity.

The predicting of the absorption coefficient (S30) is a step of predicting the absorption coefficient from the acoustic physical property value. By applying Biot's theory of mathematically modeling the elastic waves passing through the porous material, it is possible to predict the absorption coefficient for each frequency band from the acoustic physical property values of the porous material. Particularly, a reflection coefficient (R) of the porous material is calculated by using the acoustic physical property values (porosity, tortuosity, flow resistivity, thermal characteristic length, and viscous characteristic length) of the amorphous porous material calculated in the S20. Here, the reflection coefficient (R) means a sound pressure ratio between the sound wave incident on the porous material and the sound wave reflected therefrom, and finally, the absorption coefficient (α(ω)) for each frequency band of the porous material is calculated by Equation 19 below.

$$\alpha(\omega) = 1 - |R|^2 \quad \text{Equation 19}$$

As a result, the method for predicting the physical properties of the amorphous porous material according to an exemplary embodiment of the present invention has an advantage in that it is possible to predict the acoustic physical property values and the absorption coefficient which are similar to the measured values, even if not measured by the actual measurement technique through the prediction method according to an exemplary embodiment of the present invention from the parameters obtained through the three-dimensional pore connection structure.

Example

Hereinafter, the present invention will be described in more detail through the following Examples. The Examples are only examples for helping the understanding of the present invention, and the scope of the present invention is not limited thereto.

Examples 1 to 6—Amorphous Porous Material Specimens Obtained by the Pre-Shaped Product and Parameter Values Calculated According to Exemplary Embodiments of the Present Invention Obtained were Examples 1 to 6, which are specimens of the amorphous porous material of polyurethane foam from the pre-shaped product made of polyurethane foam. For example, the pre-shaped urethane foam was produced by each varying the mixing ratio of chemical additives during the foaming process. The pre-shaped urethane foam was produced by mixing isocyanate 40, 45, 50, 55, 60, and 65 wt %, respectively, based on polyol 100 wt % with regard to the mixing ratio. Examples 1 to 6, which are the specimens of the amorphous porous material, are specimens obtained from the polyurethane foams which correspond to the mixing ratio of isocyanate 40 wt % (Example 1), isocyanate 45 wt % (Example 2), isocyanate 50 wt % (Example 3), isocyanate 55 wt % (Example 4), isocyanate 60 wt % (Example 5), isocyanate 65 wt % (Example 6), respectively, and the Examples 1 to 6 have different microstructures and densities, respectively, and specific parameter analysis results are expressed in Table 1 below. A procedure of acquiring all the specimens of the amorphous porous material, respectively, is the same.

TABLE 1

| Sample | $\overline{R}_p$ [μm] | $\overline{R}_t$ [μm] | $L_{p\text{-}p}$ [μm] | $\overline{C}_n$ [—] | $\overline{\theta}_{p\text{-}p}$ [°] | $T_f$ [μm] |
|---|---|---|---|---|---|---|
| Example 1 | 236 | 115 | 342 | 7.42 | 33.02 | 12.32 |
| Example 2 | 263 | 106 | 344 | 8.46 | 29.40 | 13.60 |
| Example 3 | 239 | 97 | 329 | 8.72 | 27.58 | 13.74 |
| Example 4 | 286 | 109 | 372 | 8.23 | 30.12 | 14.92 |
| Example 5 | 263 | 123 | 383 | 8.09 | 28.53 | 14.93 |
| Example 6 | 224 | 98 | 332 | 8.01 | 27.16 | 15.72 |

Experimental Example 1—Matching Degree of the Predicted Porosity According to Exemplary Embodiments of the Present Invention and the Measured Porosity From the specimens of the amorphous porous material of the polyurethane foams according to Examples 1 to 6, the predicted porosity using the parameters obtained from the three-dimensional pore connection structure according to exemplary embodiments of the present invention and the measured porosity measured according to a porosity meter (PHI, Mecanum Inc., Canada) based on ISO 4590 were obtained, respectively. Thereafter, the matching degree was obtained by using the predicted value and the measured value.

Figure 10:
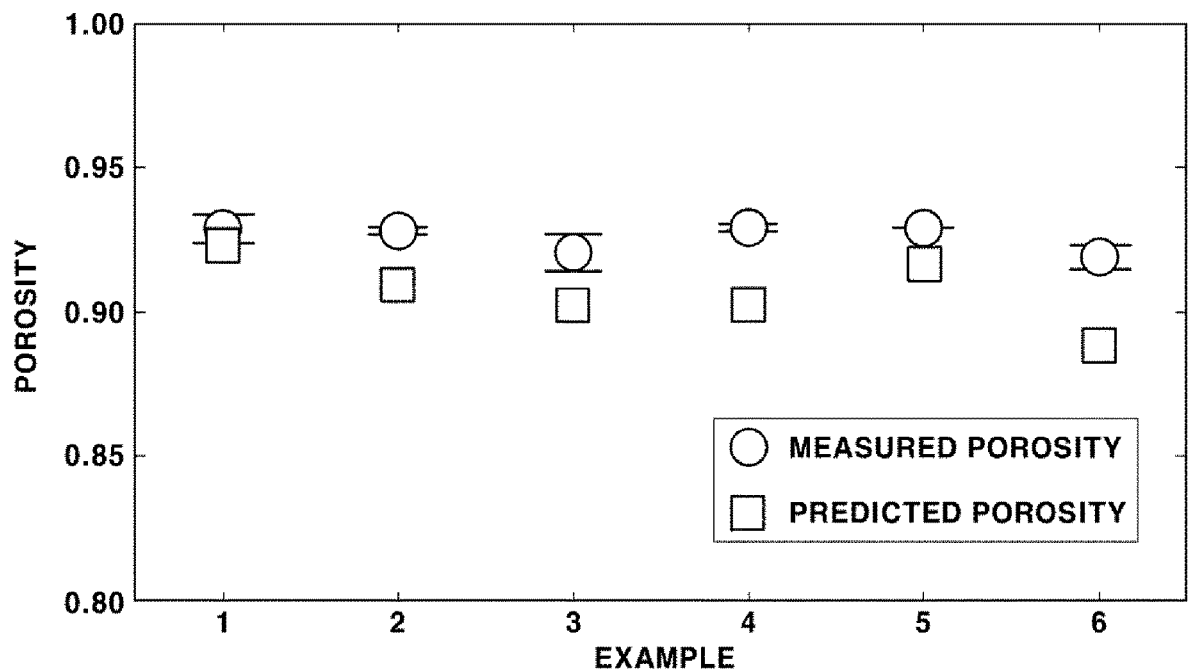
FIG. 10 shows a graph of a matching degree between a predicted porosity and a measured porosity according an exemplary embodiment the present invention, from the specimen of the amorphous porous material of polyurethane foam according to Examples 1 to 6 of the present invention.

As a result, as shown in FIG. 10, it was confirmed that for Examples 1 to 6, the predicted porosities according to an exemplary embodiment of the present invention may be estimated as values which are similar to the measured porosities within the standard deviation of 2%.

Experimental Example 2—Matching Degree of the Predicted Tortuosity According to Exemplary Embodiments of the Present Invention and the Measured Tortuosity From the specimens of the amorphous porous material of the polyurethane foams according to Examples 1 to 6, the predicted tortuosity using the parameters obtained from the three-dimensional pore connection structure according to an exemplary embodiment of the present invention and the measured tortuosity measured according to a tortuosity meter (TOR, Mecanum Inc., Canada) using ultrasonic waves were obtained, respectively. Thereafter, the matching degree was obtained by using the predicted value and the measured value.

Figure 11:
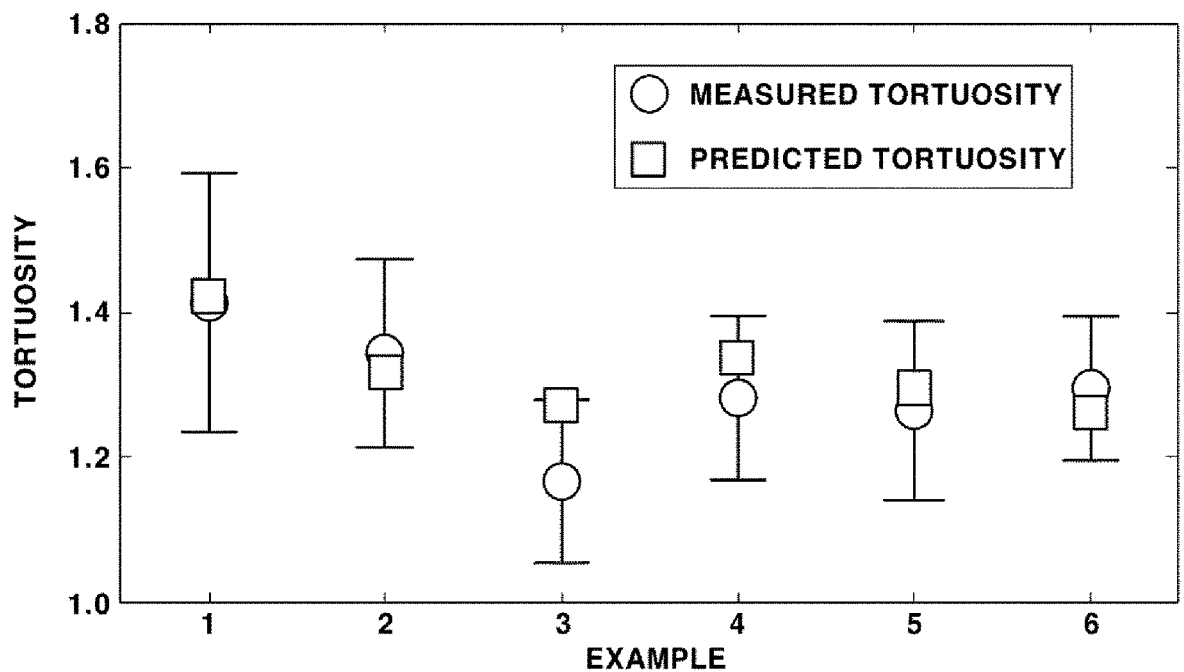
FIG. 11 shows a graph of a matching degree between a predicted tortuosity and a measured tortuosity according to an exemplary embodiment of the present invention, from the specimen of the amorphous porous material of the polyurethane foam according to Examples 1 to 6 of the present invention.

As a result, as shown in FIG. 11, it was confirmed that for Examples 1 to 6, the predicted tortuosities according to exemplary embodiments of the present invention may be estimated as values which are similar to the measured tortuosities within the standard deviation of 3%.

Experimental Example 3—Matching Degree of the Predicted Flow Resistivity According to Exemplary Embodiments of the Present Invention and the Measured Flow Resistivity From the specimens of the amorphous porous material of the polyurethane foams according to Examples 1 to 6, the predicted flow resistivity using the parameters obtained from the three-dimensional pore connection structure according to exemplary embodiments of the present invention and the measured flow resistivity measured according to an ASTM C522 reference were obtained, respectively. Thereafter, the matching degree was obtained by using the predicted value and the measured value.

Figure 12:
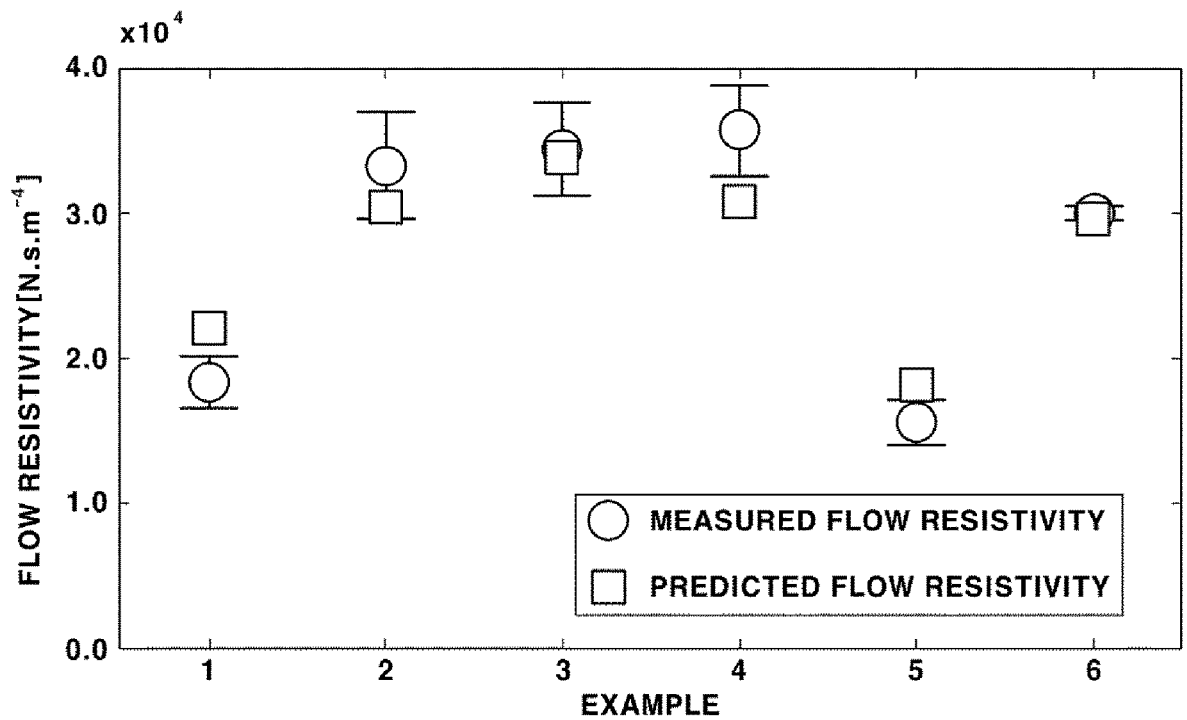
FIG. 12 shows a graph of a matching degree between a predicted flow resistivity and a measured flow resistivity according to an exemplary embodiment of the present invention, from the specimen of the amorphous porous material of the polyurethane foam according to Examples 1 to 6 of the present invention.

As a result, as shown in FIG. 12, it was confirmed that for Examples 1 to 6, the predicted flow resistivities according to exemplary embodiments of the present invention may be estimated as values which are similar to the measured flow resistivities within the standard deviation of 10%.

Experimental Example 4—Matching Degree of the Predicted Thermal and Viscous Characteristic Lengths According to Exemplary Embodiments of the Present Invention and the Thermal and Viscous Characteristic Lengths Inversely Estimated from Measured Acoustic Physical Properties From the specimens of the amorphous porous material of the polyurethane foams according to Examples 1 to 6, the predicted thermal and viscous characteristic lengths using the parameters obtained from the three-dimensional pore connection structure according to exemplary embodiments of the present invention and the thermal and viscous characteristic lengths inversely estimated by using the measured acoustic physical properties and the absorption coefficient were obtained, respectively. Thereafter, the matching degree was obtained by using the predicted value and the inversely estimated value.

Figure 13:
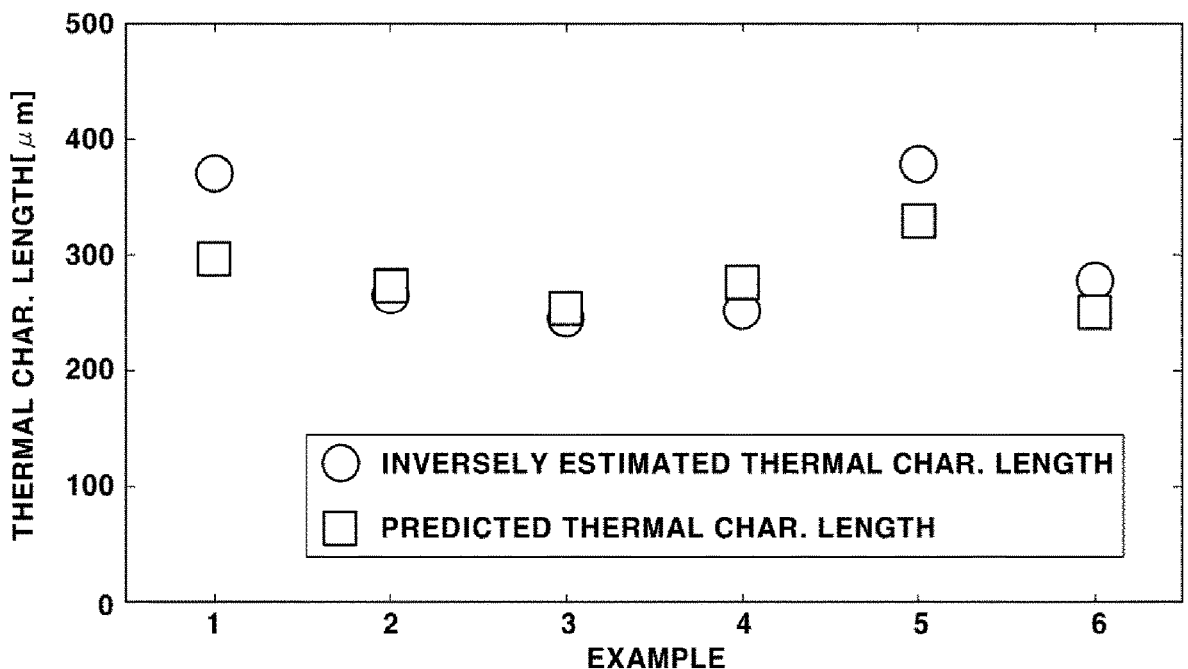
FIG. 13 shows a graph of a matching degree between a predicted thermal characteristic length and an inversely estimated thermal characteristic length according to an exemplary embodiment of the present invention, from the specimen of the amorphous porous material of the polyurethane foam according to Examples 1 to 6 of the present invention.
Figure 14:
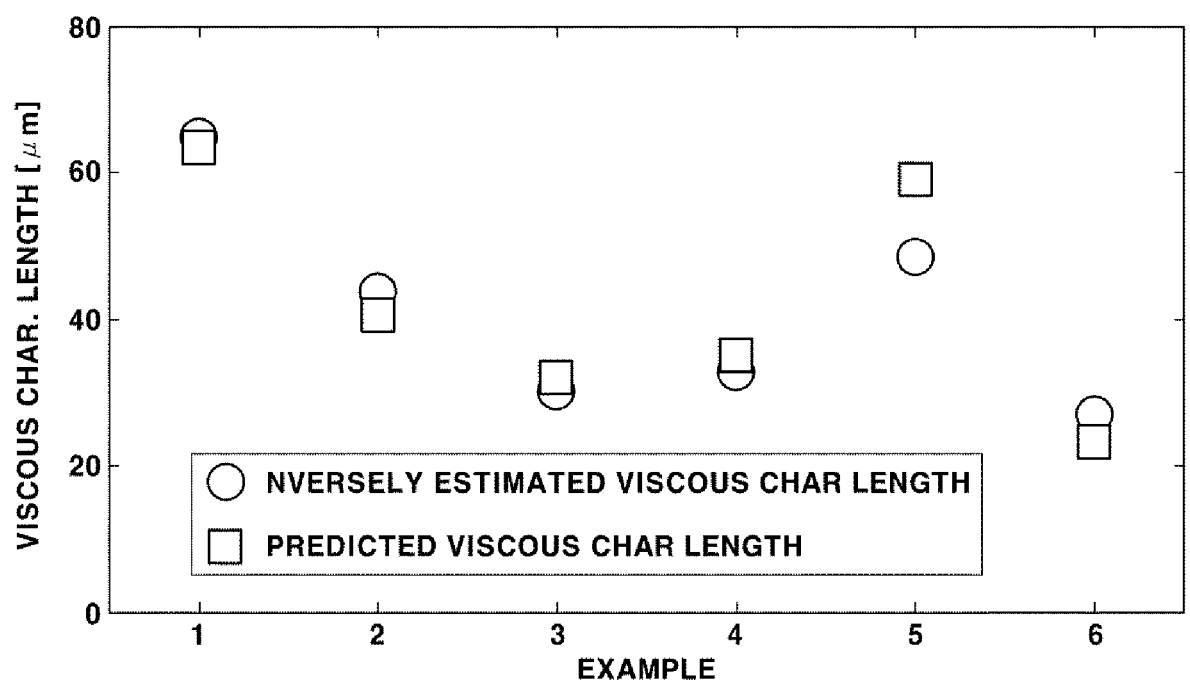
FIG. 14 shows a graph of a matching degree between a predicted viscous characteristic length and a back inversely estimated viscous characteristic length according to an exemplary embodiment of the present invention, from the specimen of the amorphous porous material of the polyurethane foam according to Examples 1 to 6 of the present invention.
Figure 15:
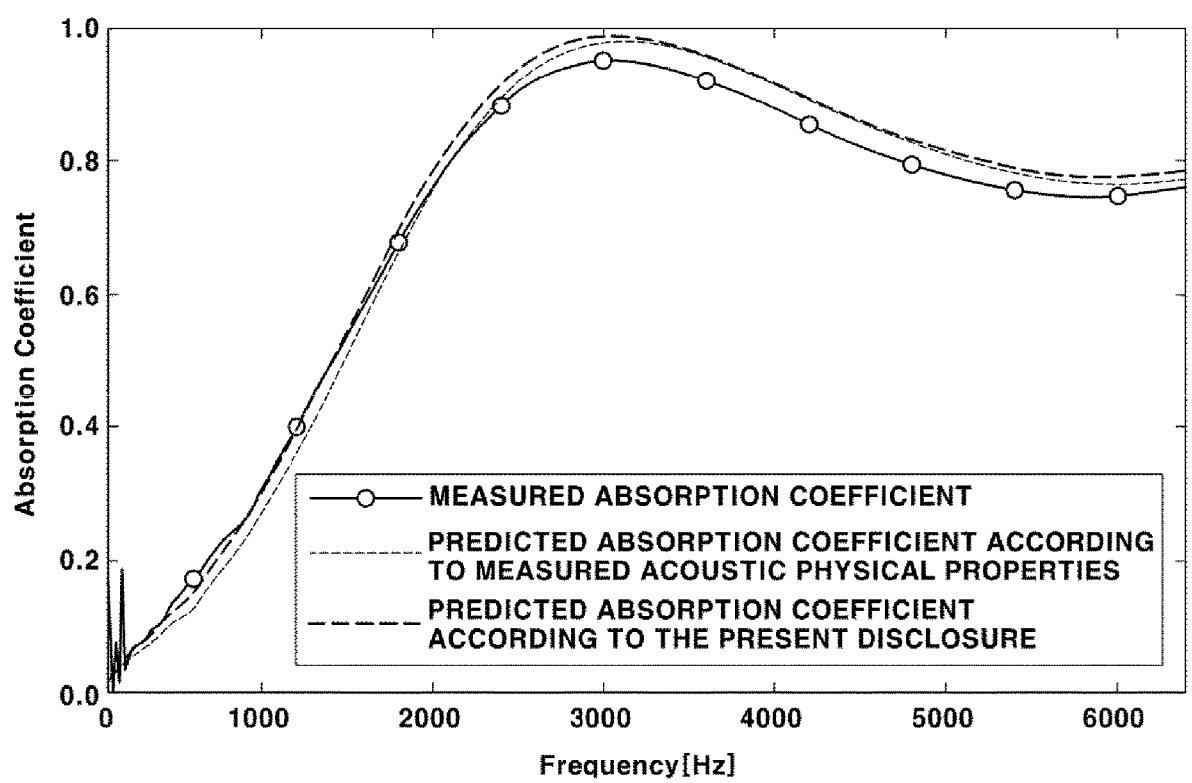
FIG. 15 shows a graph of comparing a predicted absorption coefficient according to an exemplary embodiment of the present invention, a predicted absorption coefficient according to measured acoustic physical properties, and a measured absorption coefficient, from the specimen of the amorphous porous material of the polyurethane foam according to Example 1 of the present invention.
Figure 16:
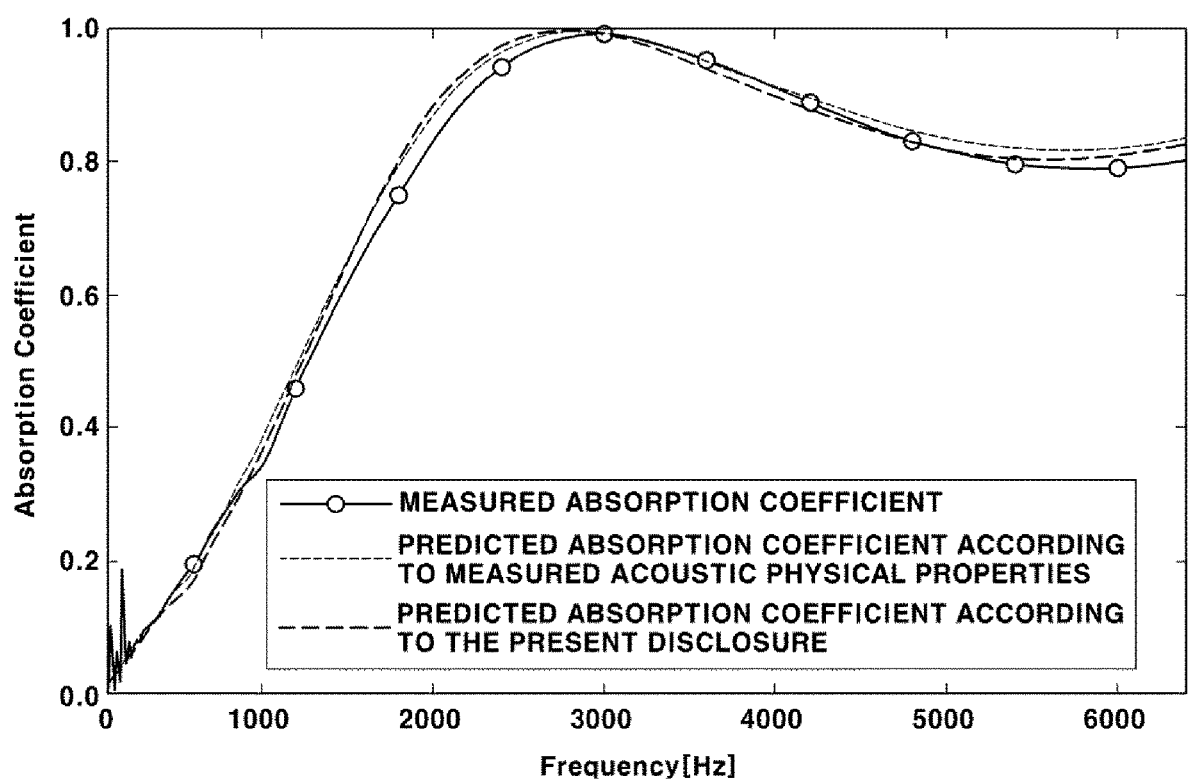
FIG. 16 shows a graph of comparing a predicted absorption coefficient according to an exemplary embodiment of the present invention, a predicted absorption coefficient according to measured acoustic physical properties, and a measured absorption coefficient, from the specimen of the amorphous porous material of the polyurethane foam according to Example 2 of the present invention.
Figure 17:
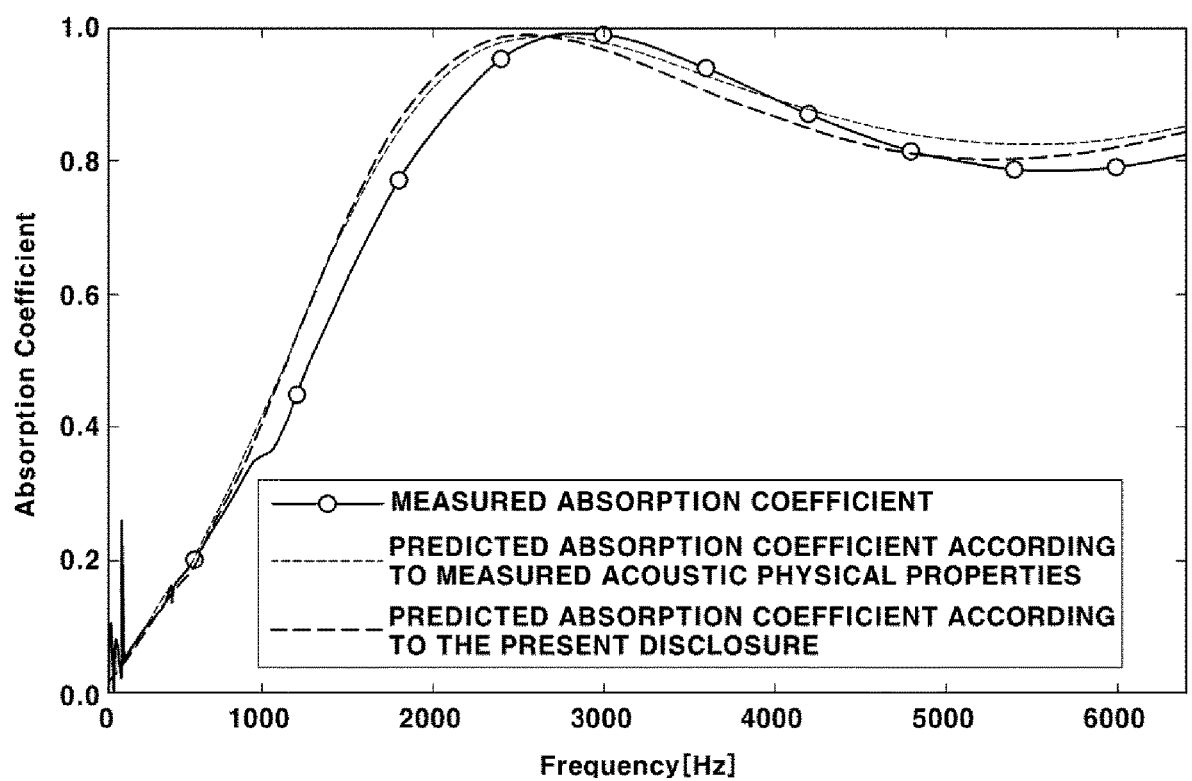
FIG. 17 shows a graph of comparing a predicted absorption coefficient according to an exemplary embodiment of the present invention, a predicted absorption coefficient according to measured acoustic physical properties, and a measured absorption coefficient, from the specimen of the amorphous porous material of the polyurethane foam according to Example 3 of the present invention.
Figure 18:
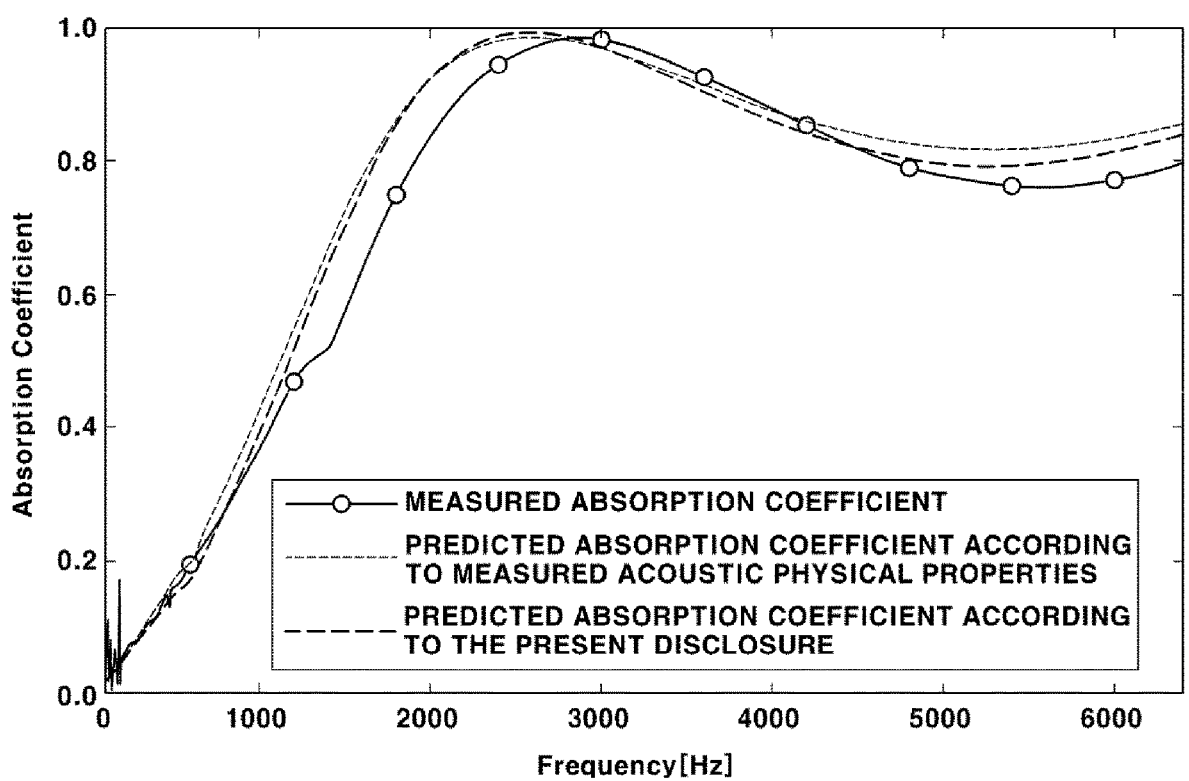
FIG. 18 shows a graph of comparing a predicted absorption coefficient according to an exemplary embodiment of the present invention, a predicted absorption coefficient according to measured acoustic physical properties, and a measured absorption coefficient, from the specimen of the amorphous porous material of the polyurethane foam according to Example 4 of the present invention.
Figure 19:
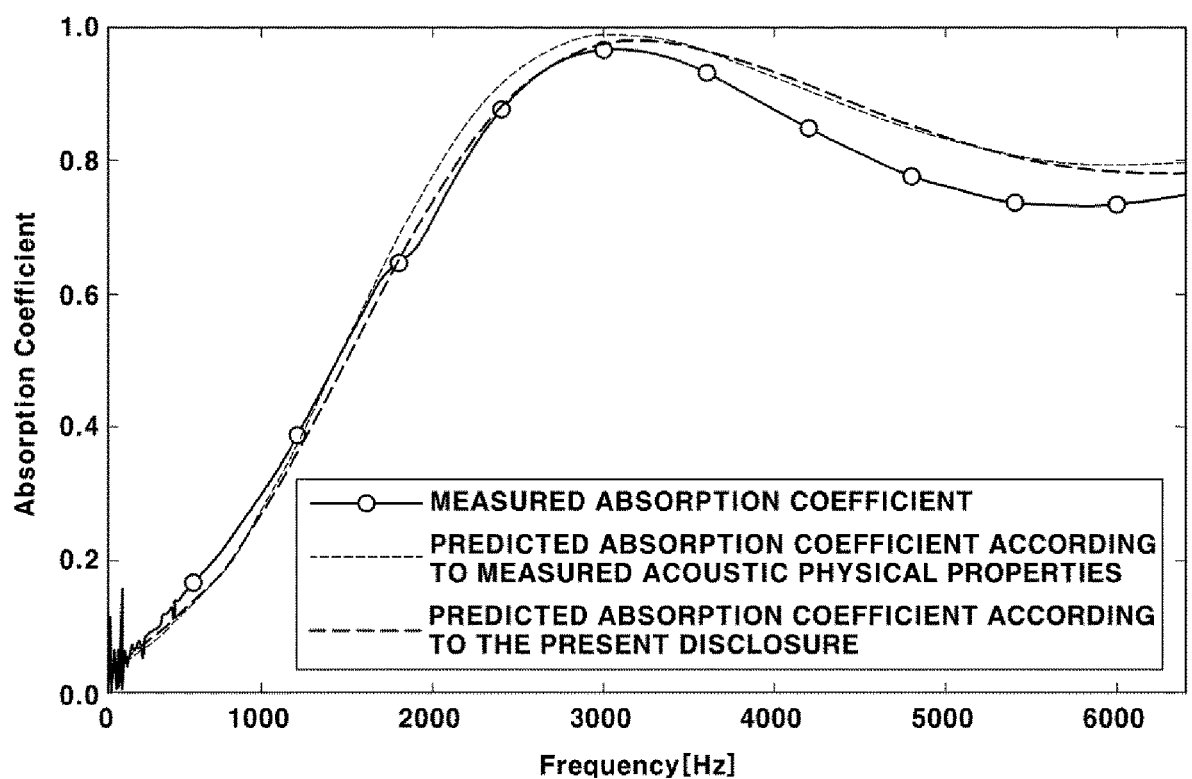
FIG. 19 shows a graph of comparing a predicted absorption coefficient according to an exemplary embodiment of the present invention, a predicted absorption coefficient according to measured acoustic physical properties, and a measured absorption coefficient, from the specimen of the amorphous porous material of the polyurethane foam according to Example 5 of the present invention.
Figure 20:
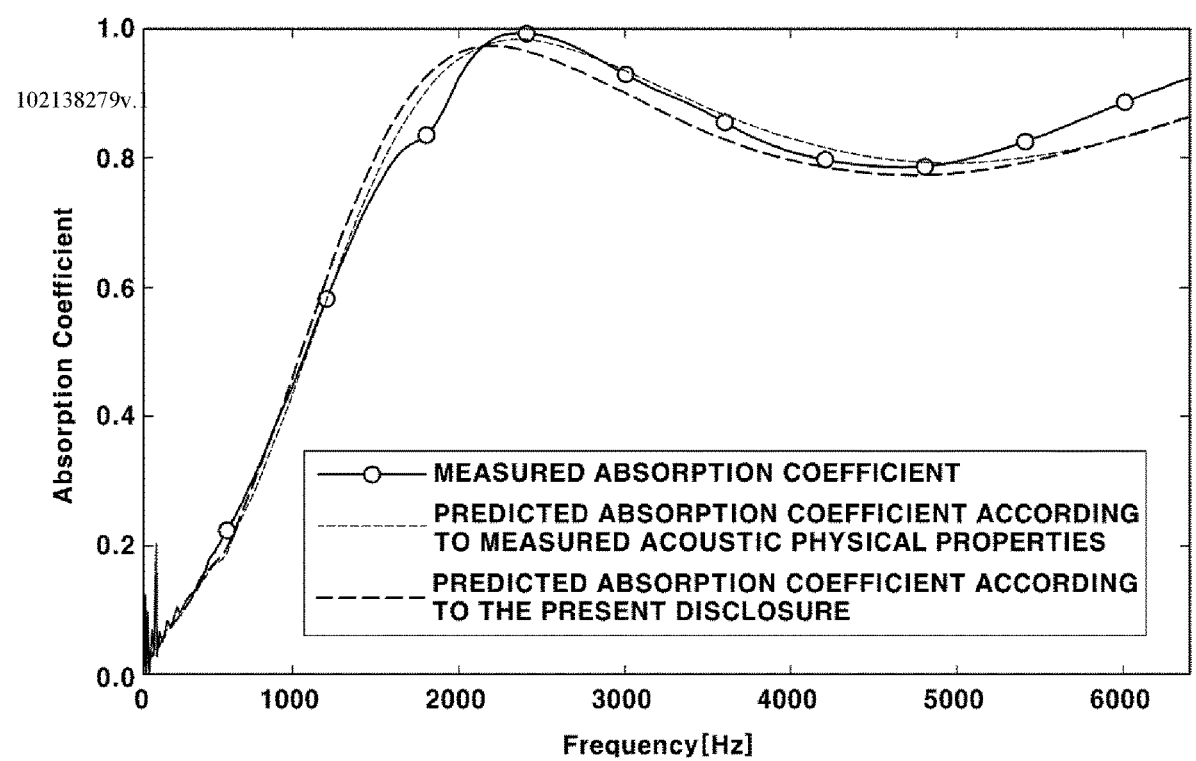
FIG. 20 is a graph of comparing a predicted absorption coefficient according to an exemplary embodiment of the present invention, a predicted absorption coefficient according to measured acoustic physical properties, and a measured absorption coefficient, from the specimen of the amorphous porous material of the polyurethane foam according to Example 6 of the present invention.

As a result, as shown in FIGS. 13 and 14, it was confirmed that for Examples 1 to 6, the predicted thermal and viscous characteristic lengths according to exemplary embodiments of the present invention may be estimated as values which are similar to the inversely estimated thermal and viscous characteristic lengths within the standard deviation of 9%.

Experimental Example 5—Comparison of the Predicted Absorption Coefficient According to Exemplary Embodiments of the Present Invention, the Predicted Absorption Coefficient According to the Measured Acoustic Physical Properties, and the Measured Absorption Coefficient From the specimens of the amorphous porous material of the polyurethane foams according to Examples 1 to 6, the absorption coefficient predicted by the acoustic physical properties predicted according to an exemplary embodiment of the present invention, the predicted absorption coefficient according to the measured acoustic physical properties measured according to Experimental Examples 1 to 4, and the measured absorption coefficient measured by using an impedance tube of the ASTM E1050 reference were obtained.

As a result, as shown in FIGS. 15 to 20, it was confirmed that for each of Examples 1 to 6, the predicted absorption coefficients according to an exemplary embodiment of the present invention may be estimated as values which are similar to the predicted absorption coefficients according to the measured acoustic physical properties and the measured absorption coefficients.

As a result, the method for predicting the physical properties of the amorphous porous material according to various exemplary embodiments of the present invention has an advantage in that it is possible to estimate the acoustic characteristics as values which are similar to the measured physical properties with the amorphous porous material which is an amorphous specimen even without separately producing the formalized specimen such as the cylindrical specimen or the flat specimen.

What is claimed is:

1. A method for predicting physical properties of an amorphous porous material, comprising:
    obtaining a parameter of an amorphous porous material; and
    calculating an acoustic physical property value of the amorphous porous material from the obtained parameter,
    wherein the parameter comprises one or more selected from the group consisting of an average pore radius ($\overline{R}_p$), an average pore throat radius ($\overline{R}_t$), an average bonding angle ($\overline{\theta}_{p-p}$) between neighboring pores, and a porous material skeleton thickness ($\overline{T}_f$), and
    wherein the acoustic physical property value comprises one or more selected from a group consisting of a porosity ($\phi$), a tortuosity ($\alpha_\infty$), a flow resistivity ($\sigma$), a thermal characteristic length ($\Lambda'$), and a viscous characteristic length ($\Lambda$).

2. The method of claim 1, further comprising predicting an absorption coefficient from the acoustic physical property value.

3. The method of claim 1 wherein the obtaining a parameter or the calculating an acoustic physical property are executed by a controller.

4. The method of claim 2 wherein the obtaining a parameter and the calculating an acoustic physical property or the predicting an absorption coefficient are executed by a controller.

5. The method of claim 1,
    wherein the obtaining of the parameter of the amorphous porous material comprises:
    obtaining the amorphous porous material from a pre-shaped product;
    obtaining a three-dimensional pore connection structure of the amorphous porous material by photographing a tomographic image of the amorphous porous material; and
    obtaining the parameter from the three-dimensional pore connection structure of the amorphous porous material.

6. The method of claim 1,
    wherein the average pore radius ($\overline{R}_P$) is obtained by calculating using Equation 1 below, $$\overline{R}_p = \frac{\int R_p \cdot f(R_p) \cdot V_p dR_p}{\int f(R_p) \cdot V_p dR_p} \quad \text{Equation 1}$$

in Equation 1, the $R_P$ refers to a pore radius, and the $V_p$ refers to a pore volume.

7. The method of claim 1,
    wherein the average pore throat radius ($\overline{R}_t$) is obtained by calculating using Equation 2 below, $$\overline{R}_t = \frac{\int R_t \cdot g(R_t) \cdot S_t dR_t}{\int g(R_t) \cdot S_t dR_t} \quad \text{Equation 2}$$

in Equation 2, the $R_t$ refers to a pore throat radius, and the $S_t$ refers to a pore throat area.

8. The method of claim 1,
wherein the average bonding angle ($\overline{\theta}_{p-p}$) between the neighboring pores is a value obtained by arithmetic averaging a frequency distribution value for each angle with the angle of degrees as a basic indicator for a bonding angle ($\theta_{i'j'}$) between the neighboring pores calculated by Equation 3 below, $$\theta_{i'j'} = \arccos\left(\frac{z_{i'} - z_{j'}}{L_{i'j'}}\right) \quad \text{Equation 3}$$

in Equation 3, the $z_i'$ and the $z_{j'}$ refer to z directional coordinate values of the neighboring i'th and j'th pores on the shortest path, and the $L_{i'j'}$ refers to a distance between the neighboring pores.

9. The method of claim 1,
wherein the porous material skeleton thickness ($T_f$) is obtained by calculating using Equation 4 below, $$T_f = \frac{2 \times r_v \times \Sigma I}{N_{v,surf}} \quad \text{Equation 4}$$

in Equation 4, the $r_v$ refers to a resolution value of the tomographic image, the $\Sigma I$ refers to a value obtained by adding all surface distance map values, and the $N_{v,surf}$ refers to the number of voxels corresponding to the surface.

10. The method of claim 1,
wherein the porosity ($\phi$) is obtained by calculating using Equation 5 below, $$\phi = \frac{V_{fluid}}{V_{fluid} + V_{solid}} \quad \text{Equation 5}$$

in Equation 5, the $V_{fluid}$ is a value calculated by Equation 6 below, and the $V_{solid}$ is a value calculated by Equation 7 below, $$V_{fluid} = \frac{4\pi}{3}\overline{R}_p^3 \times N_p \quad \text{Equation 6}$$

in Equation 6, the $\overline{R}_p$ refers to the average pore radius, and the $N_p$ refers to the number of pores, $$V_{solid} = S_{solid} \times \overline{T}_f \quad \text{Equation 7}$$

in Equation 7, the $S_{solid}$ is calculated by Equation 8 below, and the $\overline{T}_f$ refers to the porous material skeleton thickness, $$S_{solid} = 4\pi\overline{R}_p^2 - \pi\left\{\overline{R}_t^2 + \left(\overline{R}_p - \sqrt{\overline{R}_p^2 - \overline{R}_t^2}\right)\right\} \times \overline{C}_n \quad \text{Equation 8}$$

in Equation 8, the $\overline{R}_p$ refers to the average pore radius, the $\overline{R}_t$ refers to the average pore throat radius, and the $\overline{C}_n$ refers to the average pore coordination number.

11. The method of claim 1,
wherein the tortuosity ($\alpha_\infty$) is obtained by calculating using Equation 9 below, $$\alpha_\infty = \left(\frac{1}{\cos\overline{\theta}_{p-p}}\right)^2 \quad \text{Equation 9}$$

in Equation 9, the $\overline{\theta}_{p-p}$ refers to an average bonding angle between the neighboring pores.

12. The method of claim 1,
wherein the flow resistivity ($\sigma$) is calculated by Equation 10 below, $$\sigma = \frac{8\mu\alpha_\infty}{R_0^2\phi}\left[\frac{2 + 3(\delta/R_0)^2}{2(1 - (\delta/R_0)^2)^{3.5}}\right] \times \left[1 + \frac{16\pi^2}{3}\left(\frac{\delta}{\overline{L}_{p-p}}\right)^2 \frac{1 - (\delta/R_0)^2}{2 + 3(\delta/R_0)^2}\right] \quad \text{Equation 10}$$

in Equation 10, the $\mu$ refers to the viscosity of fluid (air), the $\alpha_\infty$ refers to the tortuosity, the $\phi$ refers to the porosity, the $\overline{L}_{p-p}$ refers to the average distance between the neighboring pores, the $R_0$ is calculated by Equation 11 below, and the $\delta$ is obtained by calculating using Equation 12 below, $$R_0 = (\overline{R}_p + \overline{R}_t)/2 \quad \text{Equation 11}$$

in Equation 11, the $\overline{R}_p$ refers to the average pore radius, and the $\overline{R}_t$ refers to the average pore throat radius, $$\delta = (\overline{R}_p - \overline{R}_t)/2 \quad \text{Equation 12}$$

in Equation 12, the $\overline{R}_p$ refers to the average pore radius, and the $\overline{R}_t$ refers to the average pore throat radius.

13. The method of claim 1,
wherein the thermal characteristic length ($\Lambda'$) is obtained by calculating using Equation 13 below, $$\Lambda' = 2\frac{\frac{4\pi}{3}\overline{R}_p^3}{4\pi\overline{R}_p^2 - \pi\overline{R}_t^2 \times \overline{C}_n} \quad \text{Equation 13}$$

in Equation 13, the $\overline{R}_p$ refers to the average pore radius, the $\overline{R}_t$ refers to the average pore throat radius, and the $\overline{C}_n$ refers to the average pore coordination number.

14. The method of claim 1,
wherein the viscous characteristic length ($\Lambda$) is obtained by calculating using Equation 14 below, $$\Lambda \cong \Lambda' \cdot m(\phi) = \Lambda'\left(\frac{\phi}{26(1 - \phi)}\right)^2 \quad \text{Equation 14}$$

in Equation 14, the $\Lambda'$ refers to the thermal characteristic length, and the $\phi$ refers to the porosity.

* * * * *